(12) United States Patent
Metzger

(10) Patent No.: US 8,012,216 B2
(45) Date of Patent: Sep. 6, 2011

(54) HIGH FLEXION TIBIAL TRAY

(75) Inventor: Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 273 days.

(21) Appl. No.: 12/253,255

(22) Filed: Oct. 17, 2008

(65) Prior Publication Data

US 2010/0100189 A1    Apr. 22, 2010

(51) Int. Cl.
*A61F 2/38*    (2006.01)
(52) U.S. Cl. .................................... 623/20.32
(58) Field of Classification Search .... 623/20.32–20.34, 623/14.12; *A61F 2/38*
See application file for complete search history.

(56) References Cited

U.S. PATENT DOCUMENTS

| | | | |
|---|---|---|---|
| 4,963,152 A | 10/1990 | Hofmann et al. | |
| 5,236,461 A | 8/1993 | Forte | |
| 5,344,460 A | 9/1994 | Turanyi et al. | |
| 5,609,643 A | 3/1997 | Colleran et al. | |
| 6,004,352 A * | 12/1999 | Buni | 623/20.33 |
| 6,139,581 A | 10/2000 | Engh et al. | |
| 7,025,788 B2 | 4/2006 | Metzger et al. | |
| 7,060,101 B2 | 6/2006 | O'Connor et al. | |
| 7,081,137 B1 | 7/2006 | Servidio | |
| 7,094,259 B2 * | 8/2006 | Tarabichi | 623/20.14 |
| 7,771,483 B2 * | 8/2010 | Justin et al. | 623/20.34 |
| 2003/0093156 A1 * | 5/2003 | Metzger et al. | 623/20.15 |
| 2005/0096747 A1 * | 5/2005 | Tuttle et al. | 623/20.32 |
| 2006/0142867 A1 | 6/2006 | Metzger et al. | |

* cited by examiner

*Primary Examiner* — David Isabella
*Assistant Examiner* — Jason-Dennis Stewart
(74) *Attorney, Agent, or Firm* — Harness, Dickey

(57) ABSTRACT

Various assemblies for replacing at least a proximal portion of a tibia are provided. One assembly includes a tibial tray including a superior bearing engaging surface and an inferior bone engaging surface and having a truncated posterior region; a bearing including an articulating surface, a tray mating surface, and an overhang. The tray mating surface of the bearing is in mating engagement with the inferior bone engaging surface of the tibial tray such that the overhang of the bearing extend beyond the tibial tray truncated posterior region. Related surgical methods are also provided.

7 Claims, 8 Drawing Sheets

HIGH FLEXION TIBIAL TRAY

FIELD

The present disclosure relates to a joint prosthesis and more particularly to a knee joint prosthesis having a high flexion bearing.

BACKGROUND

The statements in this section merely provide background information related to the present disclosure and may not constitute prior art.

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of flexion.

SUMMARY

The present teachings provide various assemblies for replacing at least a proximal portion of a tibia. In various embodiments, the assembly includes a tibial tray including a superior bearing engaging surface and an inferior bone engaging surface, where the tibial tray includes a perimeter side wall and a truncated posterior region; and a bearing including a superior articulating surface, an inferior tray mating surface, and an overhang, where the tray mating surface of the bearing is in mating engagement with the superior bearing engaging surface of the tibial tray such that the overhang of the bearing extends beyond the perimeter of a tibial tray sidewall at the truncated posterior region.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Referring to FIGS. 1-9C, the present teachings provide various assemblies and surgical methods useful for improving flexion of a prosthetic knee. The apparatus and surgical methods detailed herein are useful with a modular prosthesis. The increased flexion provided by the assemblies and surgical methods provides a greater range of motion and more closely mimics the natural movement of the knee. This movement is advantageous to the patient having a higher degree of freedom and use of a prosthetic implant. While various embodiments are shown in connection with a total knee replacement, it is understood that the present teachings can be incorporated into a uni-knee replacement 300 (shown in phantom on FIG. 2A).

Figure 1:
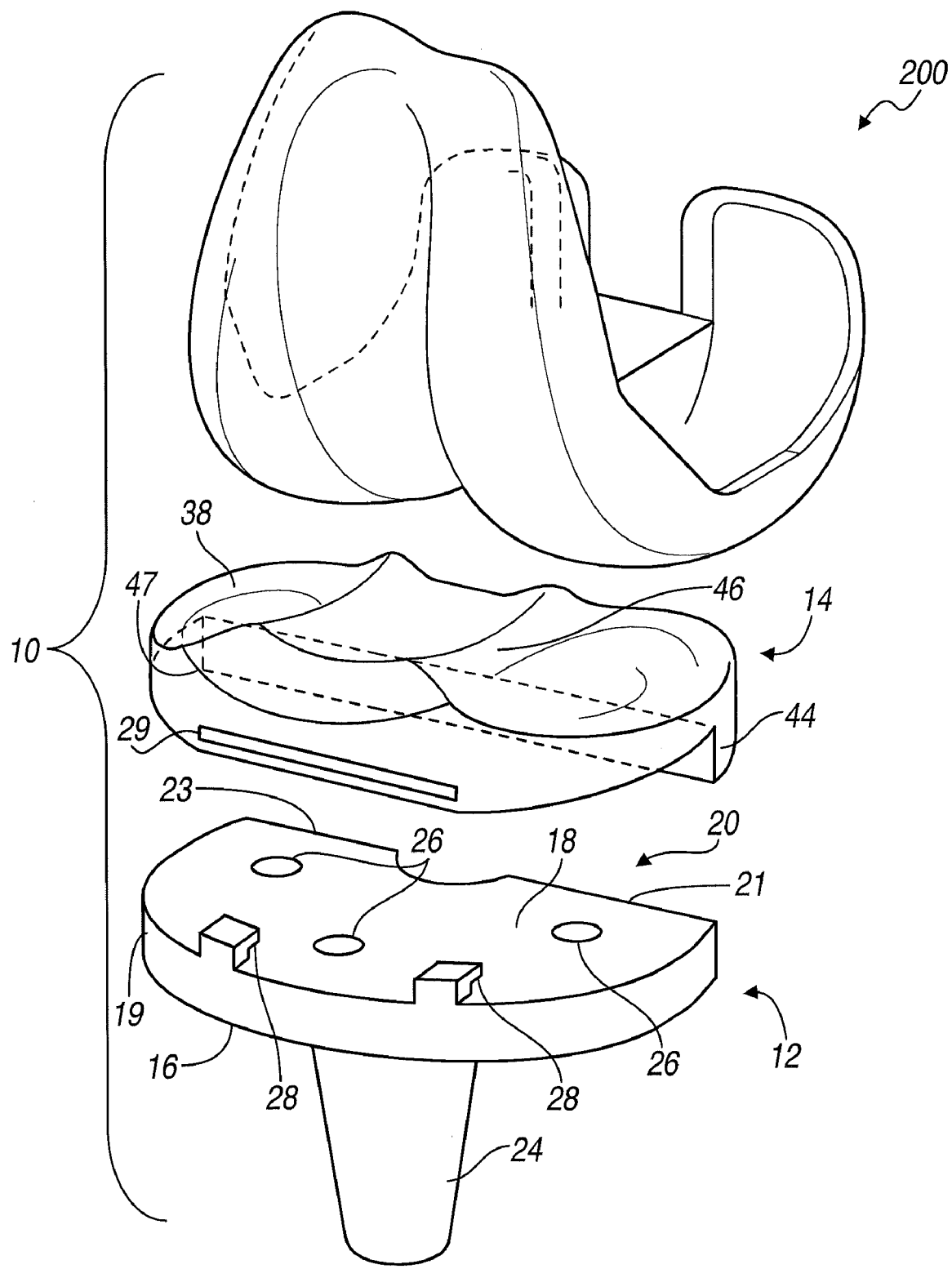
FIG. 1 depicts a perspective view of the assembly according to various embodiments of the present teachings.

Turning to FIG. 1, in various embodiments, the assembly 10 includes a tibial tray 12 and a bearing 14 to engage an articulating femoral component 200. The tibial tray 12 includes an inferior bone engaging surface 16 and a superior bearing engaging surface 18 and defines a perimeter sidewall 19. The tibial tray 12 is shaped to mate with a resected tibia 100 and can include various surface features to accommodate the specifications of the bearing 14 as detailed later herein. The tibial tray inferior bone engaging surface 16 mates with the resected tibia 100 particularly at the proximal end 102 as depicted in FIGS. 2A, 2B, and 7C.

Figure 2A:
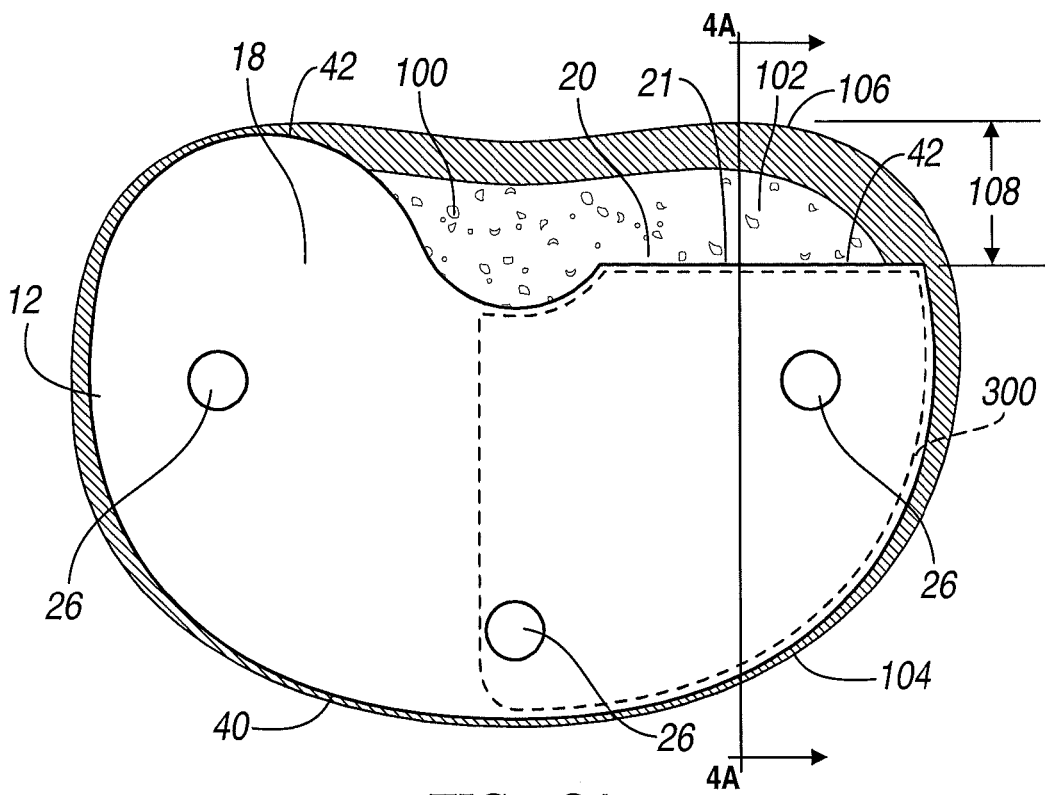
FIGS. 2A-2B depict top views of tibial trays having various truncated regions according to embodiments of the present teachings.
Figure 2B:
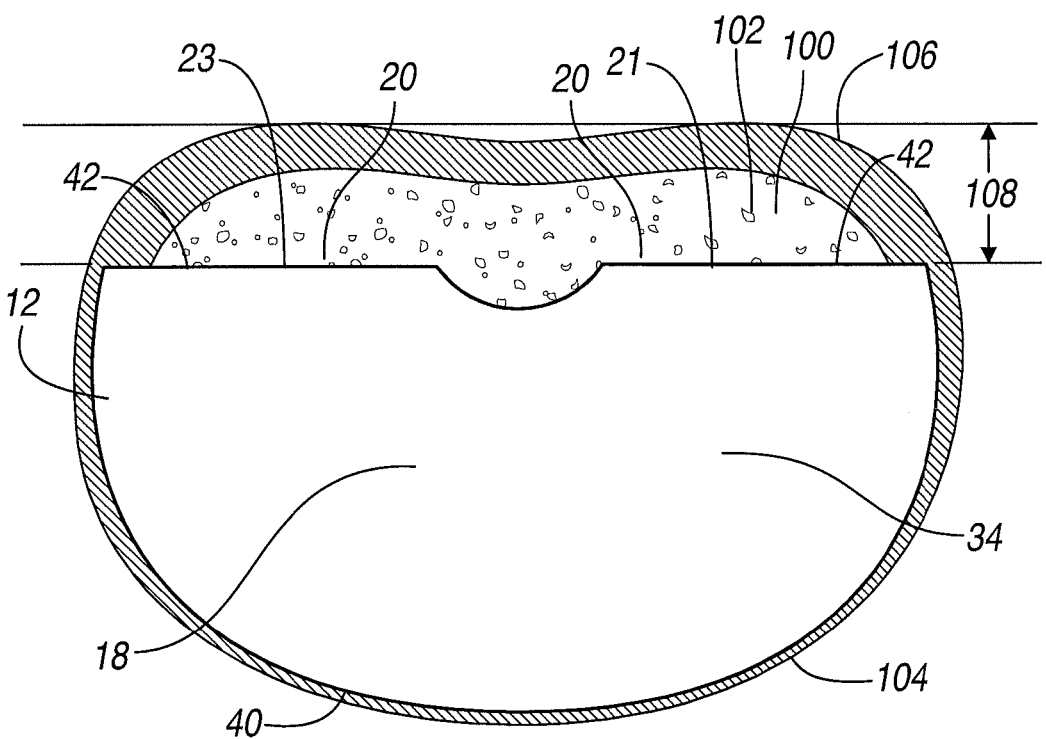

With further reference to FIGS. 2A and 2B, the tibial tray 12 is truncated such that it extends partially from an anterior end 104 of the tibia 100 towards a posterior end 106 of the tibia 100. In various embodiments, the extension is such that less than 100% of the resected tibia 100 is covered. In various other embodiments, the partial extension is such that less than 80% of the resected tibia 100 is covered. In still further embodiments, the partial extension is such that less than 65% of the resected tibia 100 is covered. The tibial tray 12 can also provide a partial extension such that less than 20% of the resected tibia is covered by the tibial tray 12. It is understood that the percentage ranges of tibial coverage disclosed include all points between. The truncated portion 20 is used to accommodate the differences in the medial and lateral condyles, such as the physical differences therebetween.

The truncated portion 20 can be on a single side of the tibial tray 12, such as the medial truncation 21 depicted in FIG. 2A. The truncated portion 20 can also be placed on both the medial and lateral side of the tibial tray 12 as shown in the medial truncation 21 and lateral truncation 23 of FIG. 2B. Aside from the truncated portions 21, 23, the tibial tray 12 is sized to fit the resected proximal end 102 of the tibia 100 and provide a substantial footprint thereon for the stability and security of the prostheses.

Figure 4A:
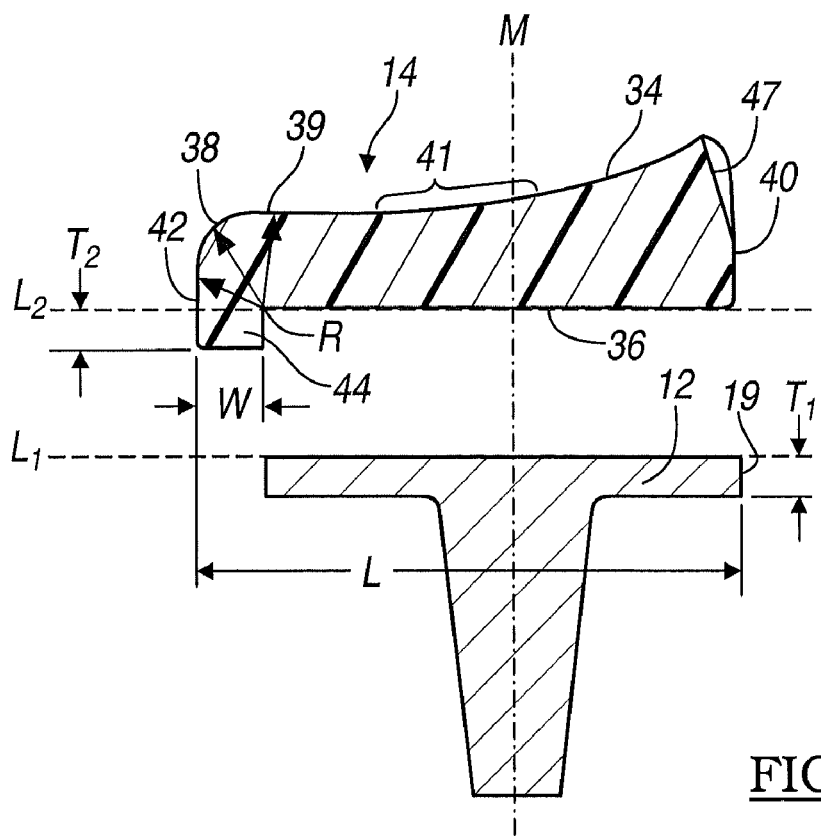
FIGS. 4A-4B depict an assembly of a bearing and truncated tibial tray taken along line 4A-4A of FIG. 2A according to embodiments of the present teachings.
Figure 4B:
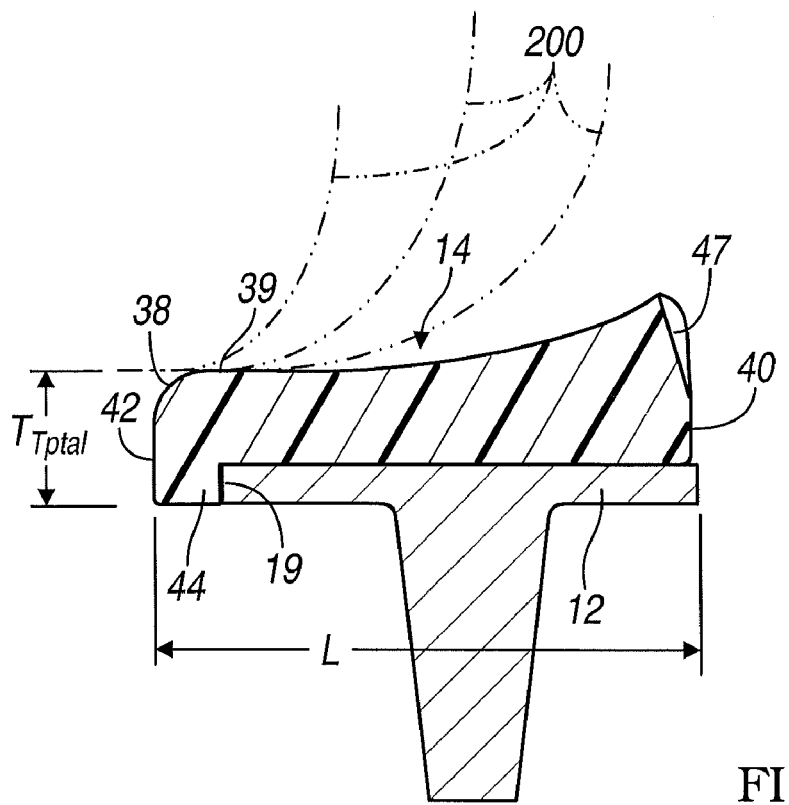
Figure 5:
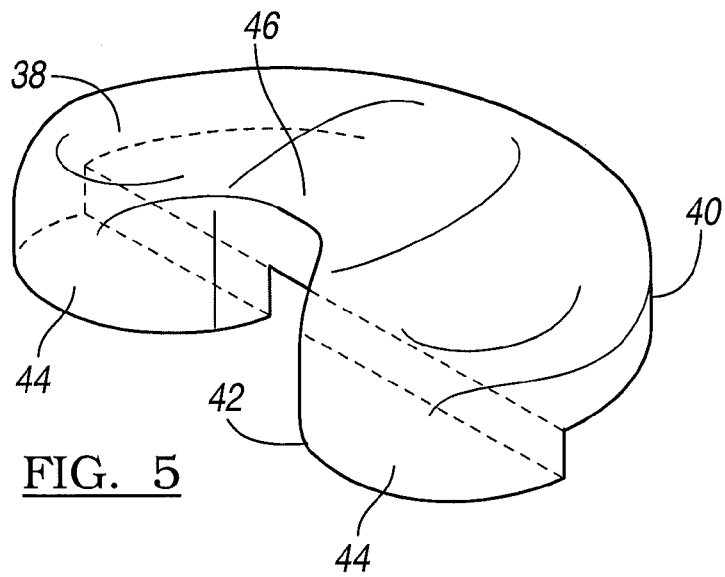
FIG. 5 depicts a perspective view of a bearing according to embodiments of the present teachings.

The tibial tray 12 has a thickness $T_1$. As shown in FIGS. 4A, 4B, and 7C, $T_1$ is constant along a substantial portion of a length L of the combined tibial tray 12 and bearing 14. The length L is taken along a sagittal plane in an anterior-posterior perspective. The thickness $T_1$ at the anterior end 40 is greater than the thickness at the posterior end 42. In other words, in various embodiments, the thickness $T_1$ at the posterior end 42 can decrease to zero. The decrease in the thickness $T_1$ of zero along the length of the assembly can indicate a truncated portion 20.

Figure 9A:
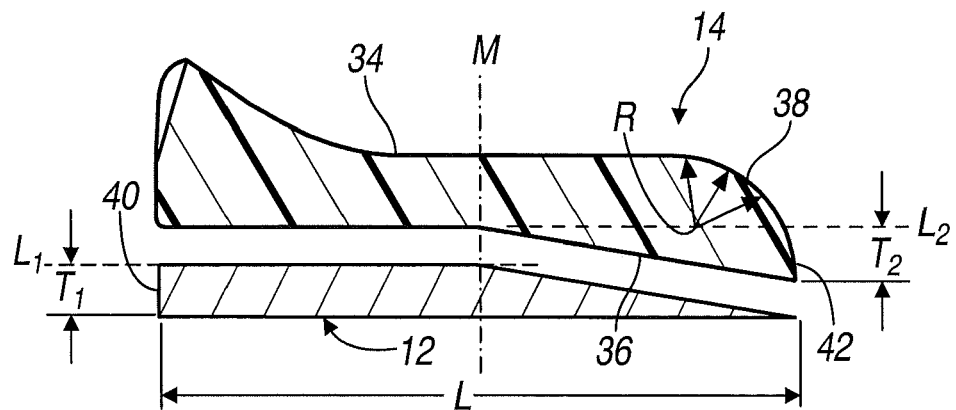
FIGS. 9A-9C depict side cross-sectional views of the assembly taken along line 4A-4A of FIG. 2A according to various embodiments of the present teachings.
Figure 9B:
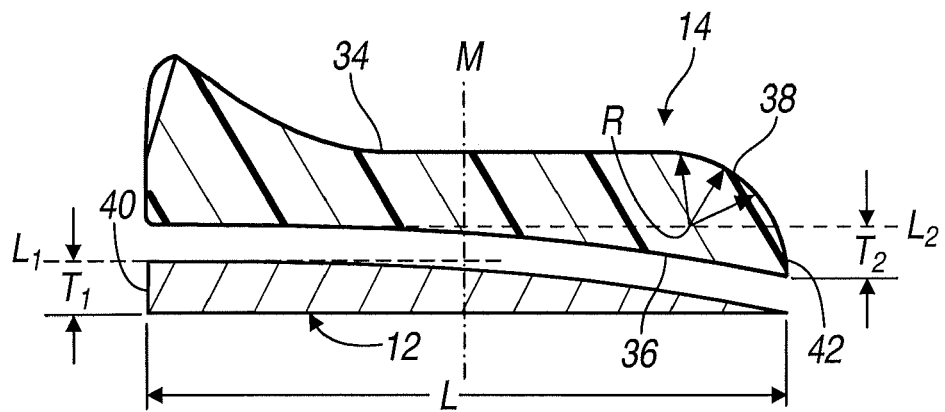
Figure 9C:
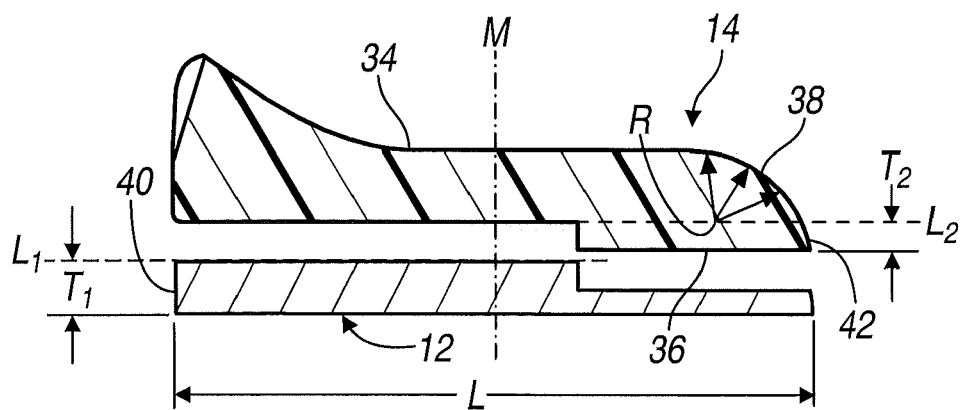

With reference to FIGS. 9A-9C, the tibial tray 12 has a varied thickness $T_1$ from an anterior end 40 of the tibial tray 12 to a posterior end 42 of the tibial tray 12 taken along a sagittal plane or along a line 4A-4A of FIG. 2A. FIG. 9A depicts a tibial tray 12 in which the thickness $T_1$ decreases from about midline M towards the posterior end 42 as a smooth linear taper. FIG. 9B depicts a tibial tray 12 in which the thickness $T_1$ decreases from about the midline M towards the posterior end 42 as a slightly curved taper. FIG. 9C depicts a tibial tray in which the thickness $T_1$ decreases from about the midline M towards the posterior end 42 as a stepped shoulder. It is understood that variations in the thickness $T_1$ along the length L of the combined tibial tray 12 and bearing 14 assembly and the point where the decrease in the tibial tray 12 thickness begins with the respect to the midline are also within the scope of the present teachings.

The tibial tray 12 can be made of any biocompatible material, including polymers, metals, and combinations thereof. Suitable exemplary metals include titanium, cobalt, chromium, or tantalum, alloys thereof, stainless steel, and combinations thereof. In still other embodiments, the tibial tray 12 can be a biocompatible polymer such as polyethylene or polyetheretherketone (PEEK).

The tibial tray 12 can also include a feature to attach the tray 12 to the tibia 100. In various embodiments, and as shown in FIG. 1, a stem 24 can be attached to the tibial tray inferior bone engaging surface 16. In still other embodiments, and as shown in FIG. 2A, the tibial tray 12 can define at least one bore 26 to receive a fastener to secure the tibial tray 12 to the tibia 100. The stem 24, the bores 26, and combinations thereof, are non-limiting examples of attachment devices and techniques. It is understood that other techniques and devices to secure the tibial tray 12 to the proximal tibia 100 are within the scope of the present teachings. As best shown in FIG. 1, the tibial tray 12 can also include a securing members 28 such as those employed in the Maxim™ Complete Knee System sold by Biomet Manufacturing, Inc. of Warsaw, Ind., United States. The securing members 28 may be used to retain the bearing surface 14 using a snap fit with the securing members 28 and an opening 29 defined in the bearing 14, as detailed later herein.

Turning to FIGS. 2A-5 and 9A-9C, the bearing surface 14 includes an articulating surface 34, a tray mating surface 36, and a rounded corner 38. The bearing 14 extends from an anterior end 40 to a posterior end 42, which generally coincide with the anterior and posterior ends of the assembly and of the proximal tibia 100. It is understood that while the tibial tray 12 in FIG. 2A references the cross-sectional view of FIG. 4A, a similar cross sectional view of the bearing 14 alone or a combination of the bearing 14 and tibial tray 12 is depicted along the same cross-sectional line at FIGS. 3A-3B, 4B, 7C, and 9A-9C. In various embodiments, such as those shown in FIGS. 2A-5, a posterior end 42 of the bearing 14 provides an overhang 44 to attach to the proximal tibial 100 with a bone cement or a fastener.

Figure 6A:
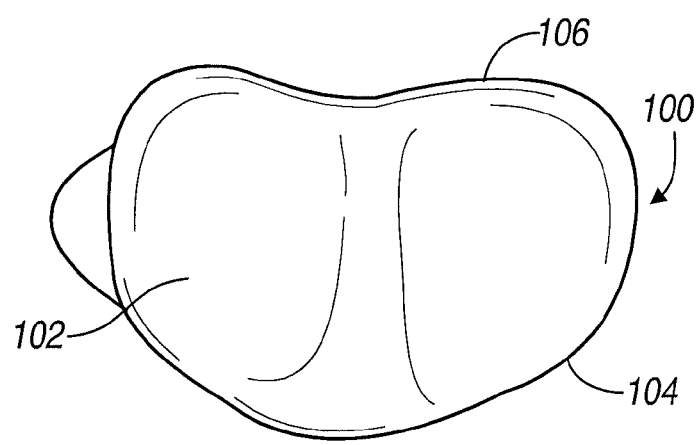
FIGS. 6A-6B depict preparation of a proximal tibia according to various embodiments of the present teachings.

As shown in FIG. 1, the articulating surface 34 of the bearing 14 mates with the femoral component 200 of the prosthesis. The bearing articulating surface 34 can include surface features 46 to mimic the natural curvature of the condyles of tibia 100 as shown in FIG. 6A. The bearing articulating surface 34 can also be shaped to mate with the particular femoral replacement 200. The scope of the present teachings includes various bearing types including a cruciate retaining knee, a posterior stabilized knee, and a fully constrained knee.

Turning to FIGS. 2A-5 and 9A-9C, the bearing 14 rounded corner 38 begins near the bearing posterior end 42 and extends downwardly from the articulating surface 34. The rounded corner 38 is down-turned towards the proximal tibia as viewed and measured relative to the sagittal plane of the body. As shown in FIGS. 3A-4A and 9A-9C, the region which defines the rounded corner provides a constant radius R as indicated by the arrows. The rounded corner 38 and adjacent regions do not include the upturned slopes, ramps, or angles provided in other bearings to provide a smooth arc for articulation.

Turning to FIGS. 9A-9C, the constant radius R is measured with respect to the dashed horizontal planar line $L_2$ to accommodate the tapering thickness $T_1$ of the tibial tray 12 from anterior end 40 to posterior end 42. Further, with respect to FIGS. 9A-9C, the thickness $T_2$ of the bearing 14 below line $L_2$ increases from the anterior end 40 towards the posterior end 42 of the bearing 14. As illustrated, the thickness $T_2$ of the bearing 14 begins increasing at about midline M towards the posterior end 42 of the combined tibial tray 12 and bearing 14. The thickness $T_1$ of the tibial tray 12 decreases from about the midline M towards the posterior end 42 of the combined tibial tray 12 and bearing 14 assembly. The tapering and increased ratio of $T_2$ to $T_1$ from about the midline M towards the posterior end 42 provide a thick and more durable bearing 14, prevent the bearing 14 from becoming too thin due to wear, and increase the natural feel of the prosthesis 10.

Advantageously, by having the rounded corner 38, a higher degree of flexion is provided as the prosthesis can roll off of the rounded corner 38 and is not confined by an upturned slope or angle. In various embodiments, where the truncated region and rounded corner 38 is at the lateral condyle, the system 10 accommodates the naturally constrained medial side and selectively allows roll-off at the lateral side. The constant radius R of the rounded corner without a ride or lip, which is on a traditional bearing, facilitates the greater range of motion and increased natural feel and movement of the implant. For example, as illustrated by the phantom lines in FIG. 4B, the femoral component 200 can have a flexion range of about 90° to about 105° degrees.

As best shown in FIGS. 3A-5, the overhang 44 extends downwardly from the rounded corner 38. The overhang 44 extends over a posterior portion of the tibial tray 12 and in use, is disposed in immediate contact with the resected proximal tibia 100. The degree of truncation of the tibial tray 12 determines the width W of the overhang 44. For example, in an embodiment where the tibial tray 12 leaves 40% of the underlying proximal tibia 100 exposed, the overhang 44 will have a greater width to approximately accommodate the missing 40%. In an embodiment where the tibial tray 12 leaves 20% of the underlying proximal tibia 100 exposed, the overhang 44 will have a smaller width to accommodate the missing 20%.

Figure 8A:
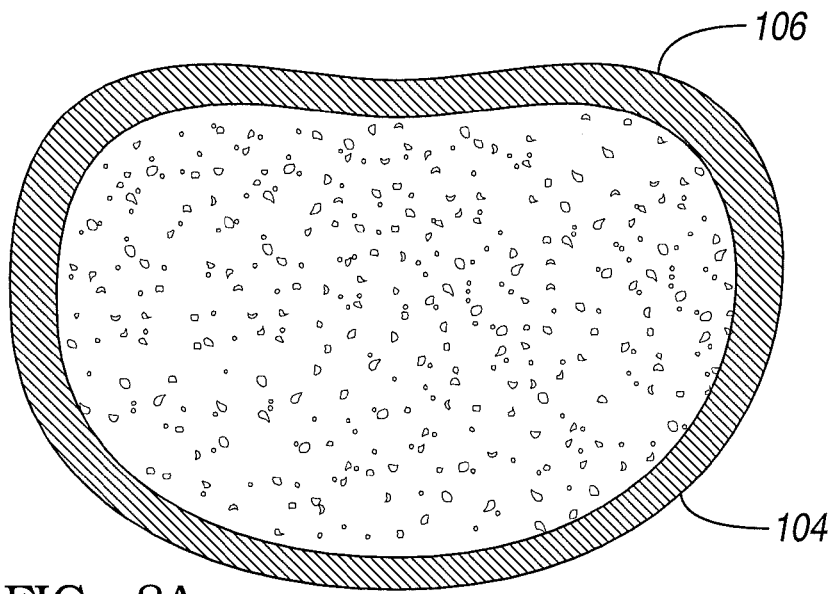
FIGS. 8A-8B depict a surgical method employing a bearing directly contacting the tibial according to various embodiments of the present teachings.
Figure 8B:
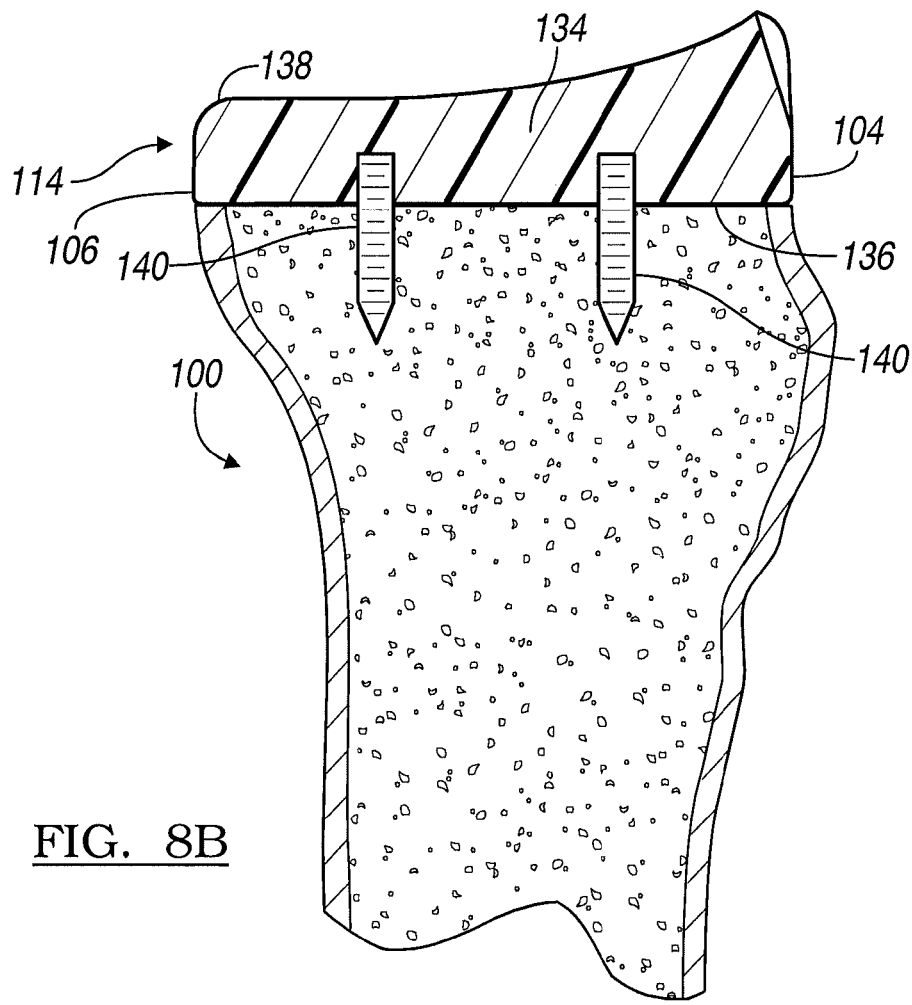

As shown in FIG. 8B, in various embodiments, a bearing 114 is designed to mate directly with the resected proximal tibia 100. The bearing 114 includes an articulating surface 134, a tibial mating surface 136, and a rounded corner 138. In such embodiments, the bearing 114 serves as both the tray and the bearing and therefore does not include an overhang such as the overhang 44 detailed above.

The bearings 14 and 114 can have a "full thickness" meaning they replace at least the thickness of the natural cartilage height. According to industry standard, a full thickness bearing has at least a 6 millimeter thickness at some point on the bearing. The bearings 14 and 114 can include at least a full thickness from the anterior edge of the assembly to the posterior edge of the resected tibia 100. In various embodiments, the bearings 14 and 114 have a varied thickness from an anterior edge 104 to the posterior edge 106 of the tibia 100. Such variations are made to mimic the contour of a natural, healthy proximal tibia 100 and the articulating surface provide therewith.

Figure 3A:
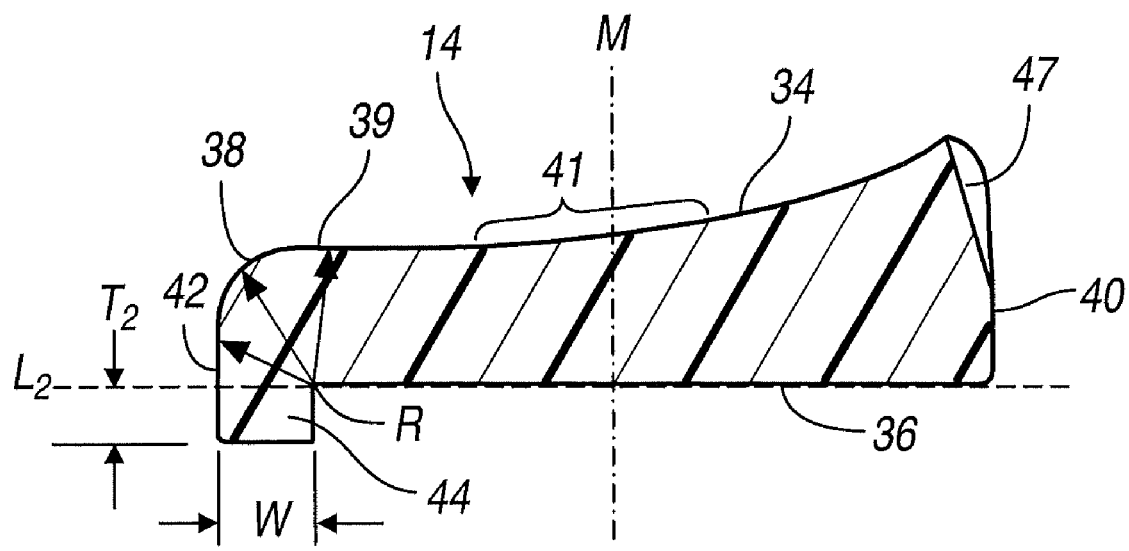
FIGS. 3A-3B depict side cross-section views of bearings taken along line 4A-4A of FIG. 2A according to embodiments of the present teachings.
Figure 3B:
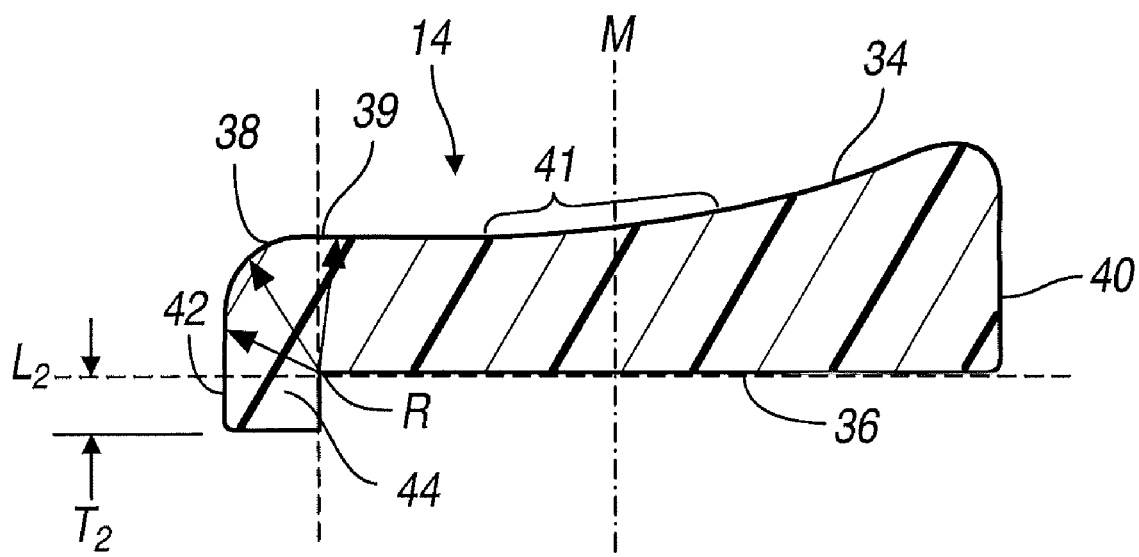

Referring to FIGS. 3A-3B, the thickness of the bearing 14 is measured from the anterior end 40 to the posterior end 42, including the thickness of the overhang 44. The thickest portion of the bearing may be at the anterior end 40, a central region 41, or at the posterior end 42. In various embodiments, the design of the overhang 44 within the bearing 14 makes the thickest portion of the bearing occur at the overhang 44, as indicated by the identifier T. The thickness is measured from a lower edge of the overhang 44 to a summit 39 of the rounded corner 38.

The increased thickness of the bearing 14 increases the cushioning on the bone and provides a greater range of flexion. The increased thickness also prevents the polymer from becoming too thin. The thick bearing 14 also provides the appropriate "roll-back" to provide a natural feeling to the prosthetic.

In various embodiments, the bearing 14 or 114 can be made of a biocompatible polymer. Suitable polymers are long-wearing for the particular application and have a sufficiently low coefficient of friction to provide smooth articulation for the patient. An exemplary suitable polymer is an ultra high molecular weight polyethylene or polyetheretherketone (PEEK).

Turning to FIGS. 6A-8B, the present teachings provide methods of replacing a proximal end of the tibia 100. First, the proximal end 102 of the tibia 100 is resected from the anterior end 104 to the posterior end 106 along the dotted line. The resection can be conducted in any suitable manner, such as using a saw and cutting guide, for example, as is well-known in the art.

Figure 7A:
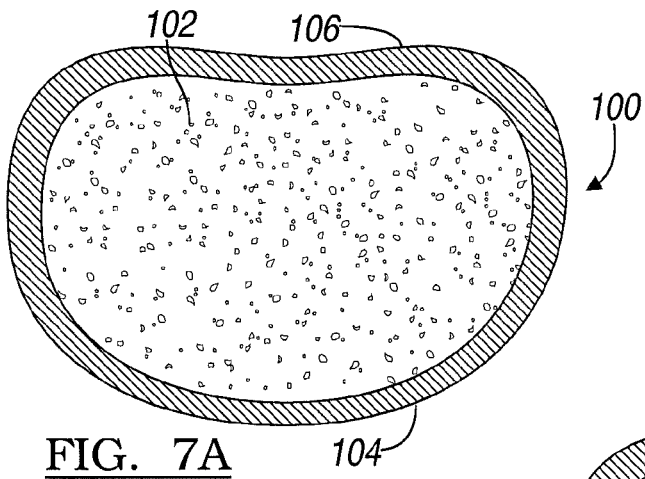
FIGS. 7A-7C depict a surgical method employing a tibial tray and bearing according to various embodiments of the present teachings.
Figure 7B:
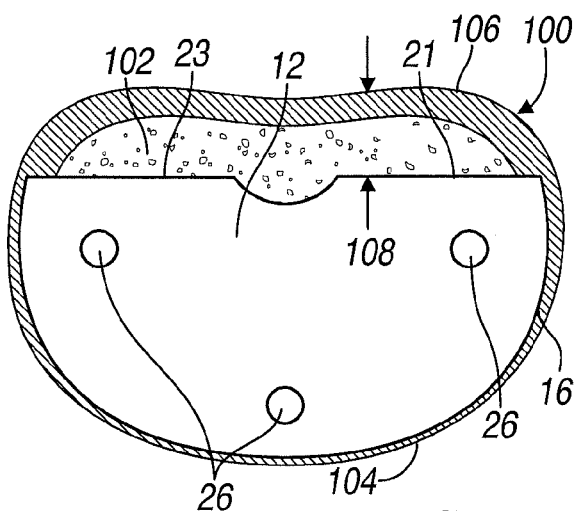
Figure 7C:
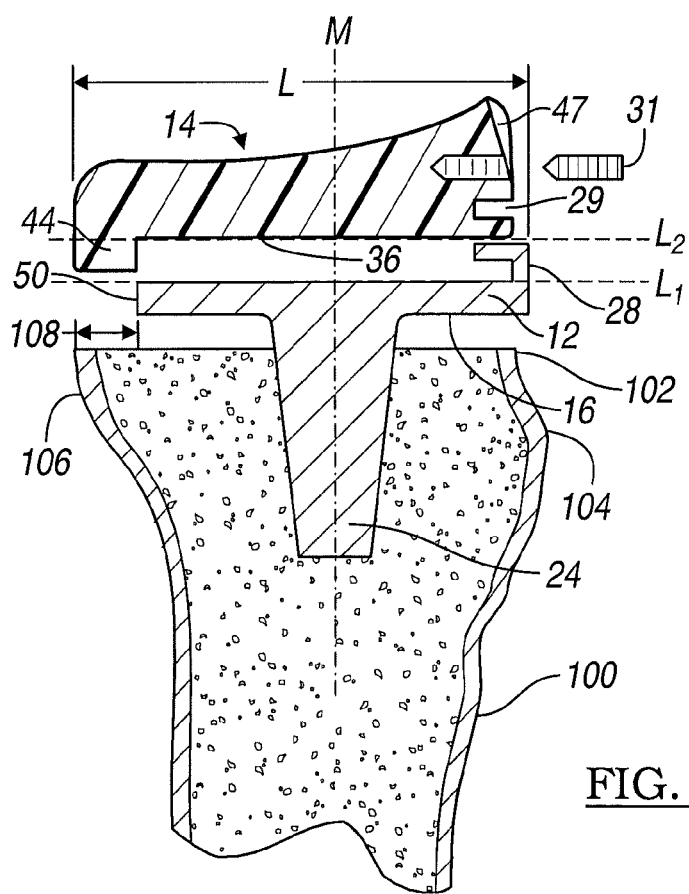

In embodiments using a tibial tray 12, as shown in FIGS. 7A-7C, the inferior bone engaging surface 16 of the tibial tray 12 is placed in mating engagement with the resected tibia 100. As best illustrated in FIG. 7B, the truncated region 21 of the tibial tray 12 leaves an exposed posterior section of the tibia 100 which is not covered by the tibial tray 12. The exposed posterior section 108 provides the location for the direct contact between the bearing 14 and the tibia 100.

Turning to FIG. 7C, the tibial tray 12 is then optionally secured to the tibia 100. In embodiments employing a stem 24 as shown in FIG. 1, the stem 24 is passed through a pre-drilled hole in the tibia 100 and can be further secured with a bone cement. Fasteners can be attached in the fastener openings or bores 26 as shown in FIG. 2A to fix the tibial tray 12 to the tibia 100. In various embodiments, other surgical techniques can be employed in addition to or in place of the fasteners to secure the tray 12 to the tibia 100. Returning to FIG. 7C, the securing element 28 can be mated to a recess 29 or notch in the bearing 14 to provide a keyed fit. In the depicted embodiment, securing element 28 comprises a lip. The recess 29 and the lip-type securing element 28 can be locked together by the keyed fit or with a fastener 31 which is placed in a passage formed by the bearing 14 and the tibial tray 12.

The tibial tray mating surface 36 of the bearing 14 is then disposed on the tibial tray 12 to place the bearing 14 and the tibial tray 12 in mating engagement. The overhang 44 abuts ledge 50 as formed between the tibial tray 12 and the exposed bone 108. As shown best in FIG. 4B, when the tibial tray 12 and the bearing 14 are in mating engagement, the lower surface of the mated combination forms a planar surface to abut the underlying proximal tibia 100. The overhang 44 is in direct contact with the underlying proximal tibia 100. The bearing 14 can also be secured to the tibial tray 12 using an adhesive or with mechanical devices such as a fastener. In various embodiments, the bearing 14 can include a mated feature such as a dove-tail or a locking ring which mates with the same opposed feature on the tibial tray 12, such as the lip 28 detailed above and depicted in FIG. 1.

Figure 6B:
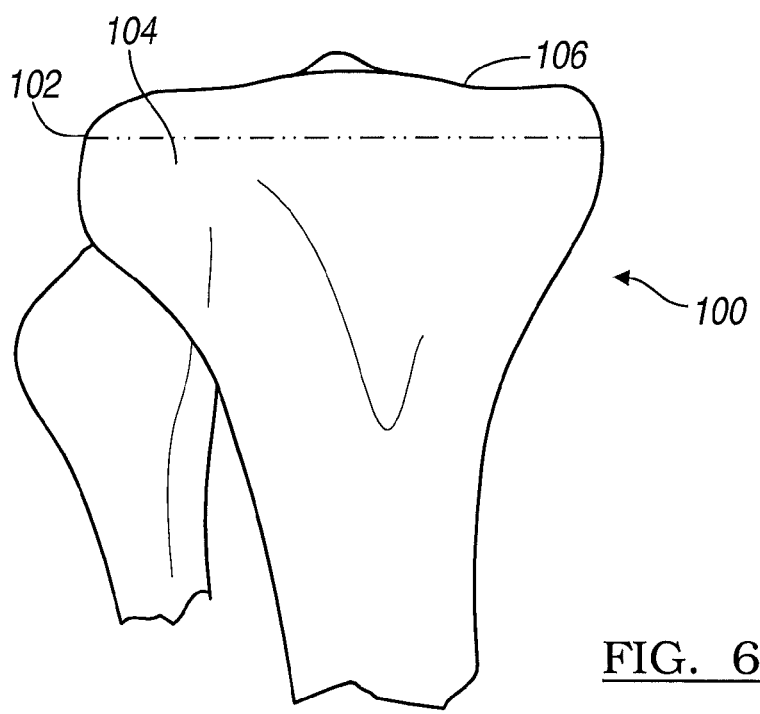

Turning to FIGS. 8A and 8B, in embodiments employing the bearing 114, the tibia 100 is resected and prepared as detailed above and shown in FIGS. 6A and 6B. The surface 136 of the bearing 114 is then placed directly on the resected tibia 100. The bearing 114 can be attached using an adhesive or using a fastener such as those detailed above. In embodiments having a fastener, a post 140, as illustrated in FIG. 8B, can be embedded into the bearing 114 or molded into the bearing 114. The thickness of the bearing 114 provides the necessary cushioning and appropriate load on the cortex.

In either embodiments of FIGS. 7A-7C, FIGS. 8A-8B, or FIGS. 9A-9C, the placement of the bearing 14 and 114, respectively, provide the rounded corner 38, 138 respectively, in the appropriate position to facilitate high flexion through the roll-off.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. An assembly having an assembly length as measured along a sagittal plane for replacing at least a proximal portion of a tibia comprising:
   a. a tibial tray having a superior surface and an inferior surface and having a thickness $T_1$; and
   b. a bearing having a superior surface, an inferior surface, and a rounded corner at a posterior end of the bearing having a constant radius as measured from a sagittal plane, wherein the bearing has a thickness of $T_2$,
   wherein the ratio of $T_2$ to $T_1$ continuously increases from about a midline of the assembly length to a posterior end of the tibial tray.

2. The assembly according to claim 1, wherein $T_1$ decreases to 0 at a posterior end of the assembly length.

3. The assembly of claim 2, wherein $T_2$ correspondingly increases to have a thickness at the posterior end equal to thickness $T_1$ of the bearing at an anterior end.

4. The assembly according to claim 1, wherein $T_2$ has a minimum thickness of about 6 millimeters.

5. The assembly of claim 1, wherein the ratio of $T_2$ to $T_1$ increases linearly from about a midline of the assembly length in a direction from an anterior end towards a posterior end of the tibial tray.

6. An assembly having an assembly length as measured along a sagittal plane for replacing at least a proximal portion of a tibia comprising:
   a. a tibial tray having a superior surface and an inferior surface, a first thickness at an anterior end and a second thickness at a posterior end; and
   b. a bearing having a superior surface, an inferior surface, a rounded corner at a posterior end of the bearing having a constant radius transitioning from the superior surface to a perimeter sidewall at the posterior end between the superior surface and the inferior surface as measured from a sagittal plane, and an overhang having a third thickness;

wherein the thickness of the tibial tray decreases from the first thickness to the second thickness in a stepped manner between a midline of the assembly length and the posterior end of the tibial tray;

wherein the inferior surface of the bearing is in mating engagement with the superior surface of the tibial tray such that the overhang engages an area of the tibial tray having the second thickness.

7. The assembly of claim 6, wherein the third thickness of the bearing overhang corresponds to a difference in thickness between the first thickness and the second thickness of the tibial tray.

* * * * *

UNITED STATES PATENT AND TRADEMARK OFFICE
CERTIFICATE OF CORRECTION

| | | |
|---|---|---|
| PATENT NO. | : 8,012,216 B2 | Page 1 of 1 |
| APPLICATION NO. | : 12/253255 | |
| DATED | : September 6, 2011 | |
| INVENTOR(S) | : Robert Metzger | |

It is certified that error appears in the above-identified patent and that said Letters Patent is hereby corrected as shown below:

Title Page, Item (57), Abstract, Line 9, "extend" should be --extends--.

Column 2, line 2, "tibial" should be --tibia--.

Column 2, line 25, "on" should be --in--.

Column 3, line 19, after "with", delete "the".

Column 3, line 40, after "include", delete "a".

Column 3, line 59, "tibial" should be --tibia--.

Column 5, lines 6-7, "provide" should be --provided--.

Signed and Sealed this
Twenty-ninth Day of November, 2011

David J. Kappos
*Director of the United States Patent and Trademark Office*